United States Patent [19]

Scheller

[11] Patent Number: 4,626,248
[45] Date of Patent: Dec. 2, 1986

[54] OPHTHALMIC CASSETTE

[75] Inventor: Gregg D. Scheller, St. Peters, Mo.

[73] Assignee: Storz Instrument Company

[21] Appl. No.: 809,118

[22] Filed: Dec. 16, 1985

[51] Int. Cl.[4] ............................................. A61M 1/00
[52] U.S. Cl. .................................. 604/319; 604/323; 604/119; 128/762
[58] Field of Search ..................... 604/22, 34, 35, 317, 604/319, 320, 323, 324, 325; 128/760, 762, 766

[56] References Cited

U.S. PATENT DOCUMENTS

| | | | |
|---|---|---|---|
| 3,866,608 | 2/1975 | Reynolds et al. | 604/319 |
| 4,475,904 | 10/1984 | Wang | 604/119 |
| 4,493,695 | 1/1985 | Cook | 604/27 |
| 4,493,698 | 1/1985 | Wang et al. | 604/119 |

Primary Examiner—Stephen C. Pellegrino
Assistant Examiner—John D. Ferros
Attorney, Agent, or Firm—Harness, Dickey & Pierce

[57] ABSTRACT

The replaceable cassette is integrally formed with a small primary container for fast response time when aspirating, and an integrally formed, larger secondary container into which the contents of the primary container are periodically flushed. During aspiration, the secondary container is sealed from the primary container and, therefore, has no adverse effect on aspiration response time. The primary container is located above the secondary container and the two containers are connected by a standpipe through which substances are flushed by the force of gravity in emptying the contents of the primary container into the secondary container. Although the cassette will operate with microsurgical consoles having two separate vacuum sources, only one vacuum source is required.

20 Claims, 11 Drawing Figures

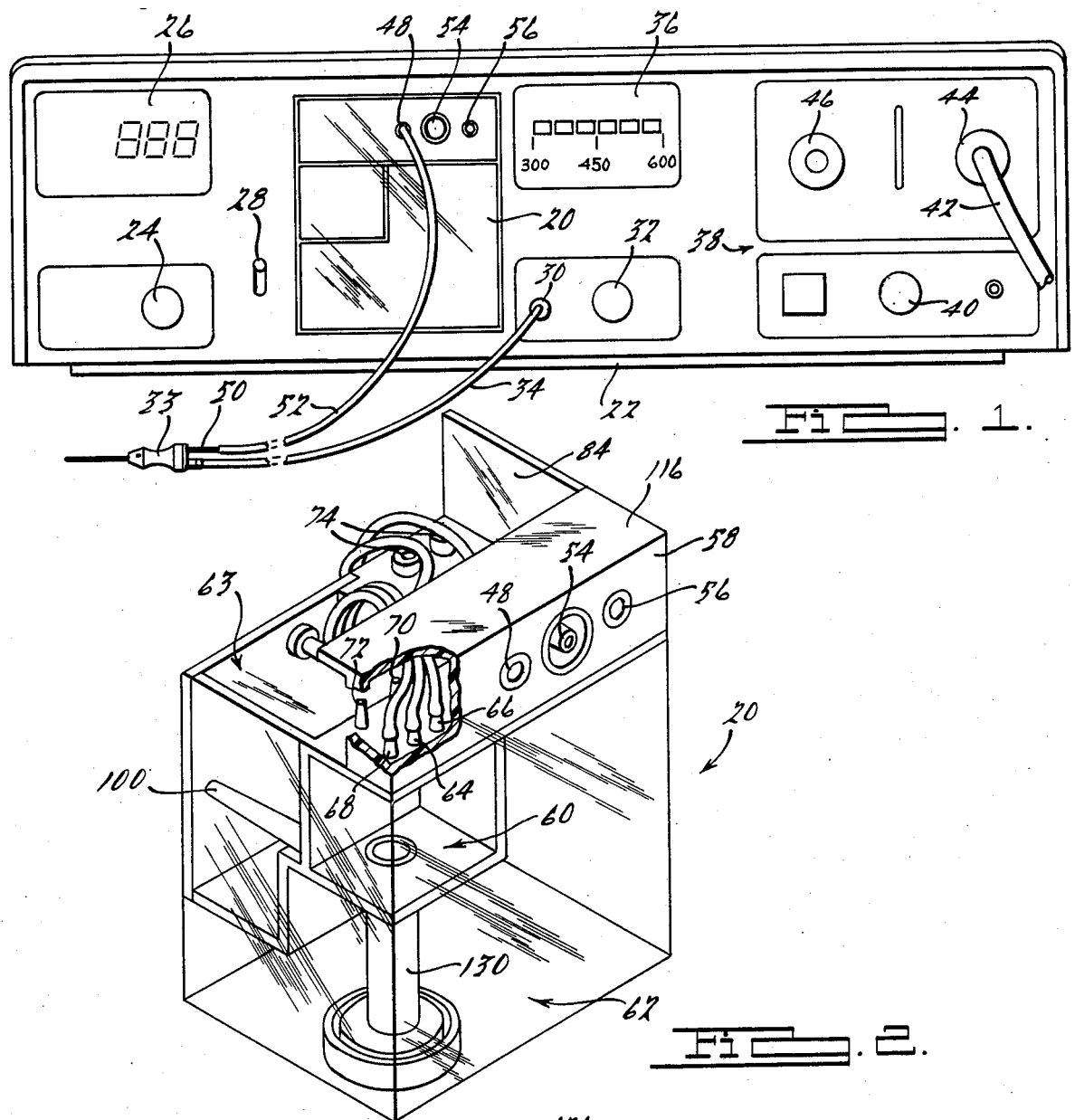
Fig. 1.
Fig. 2.
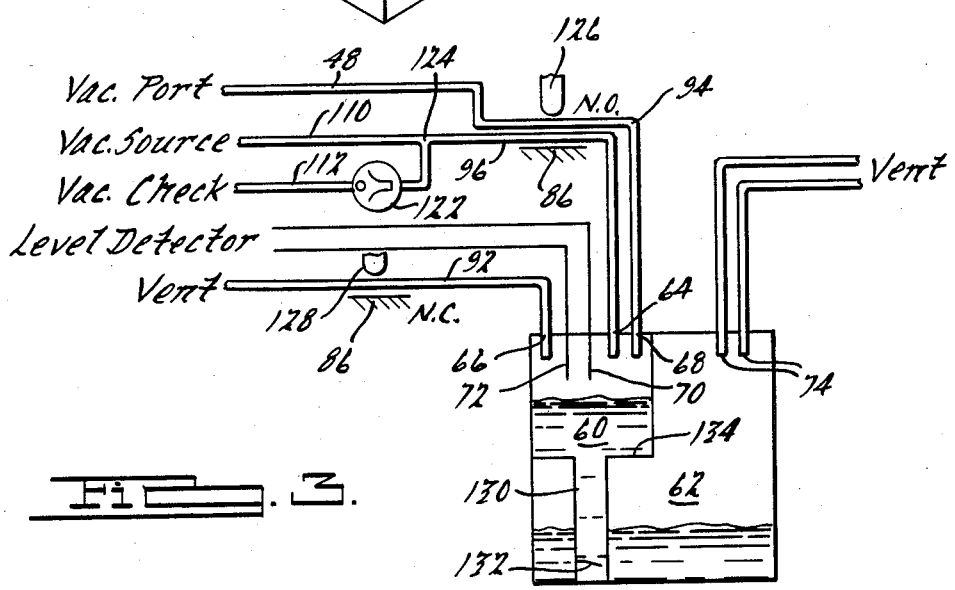
Fig. 3.

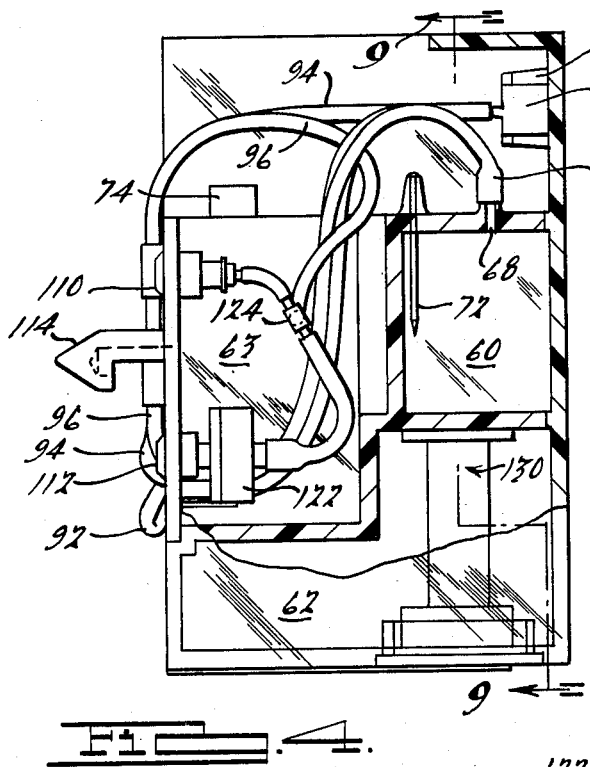
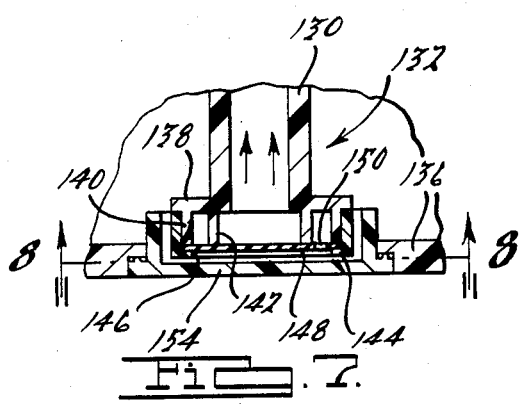
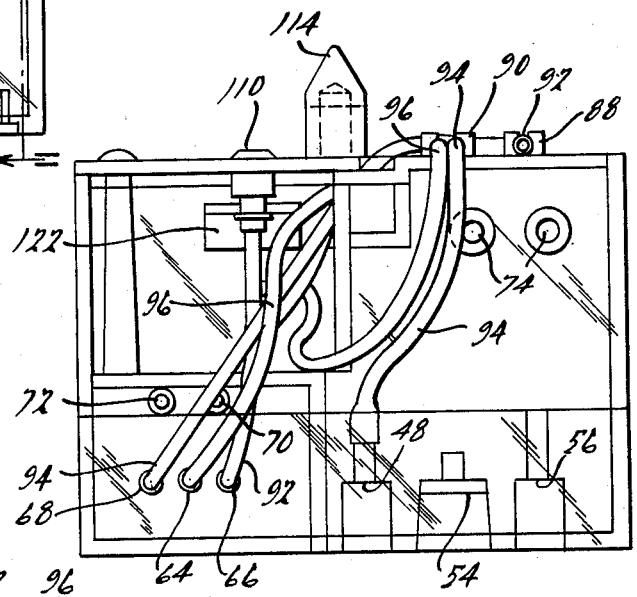
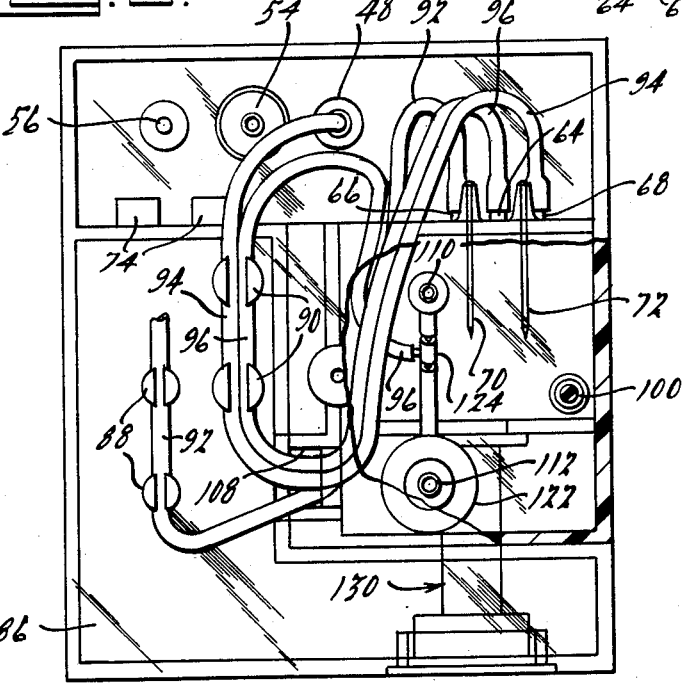
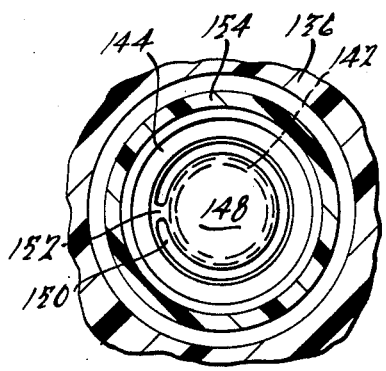

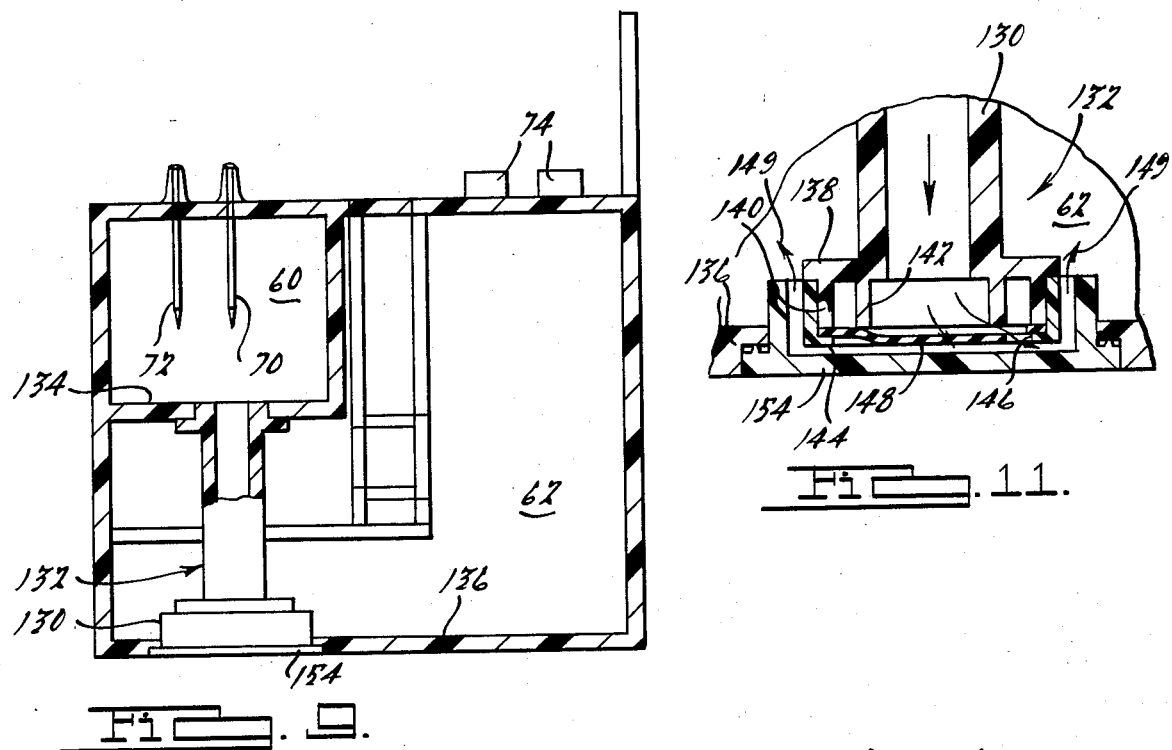
Fig. 9.
Fig. 11.
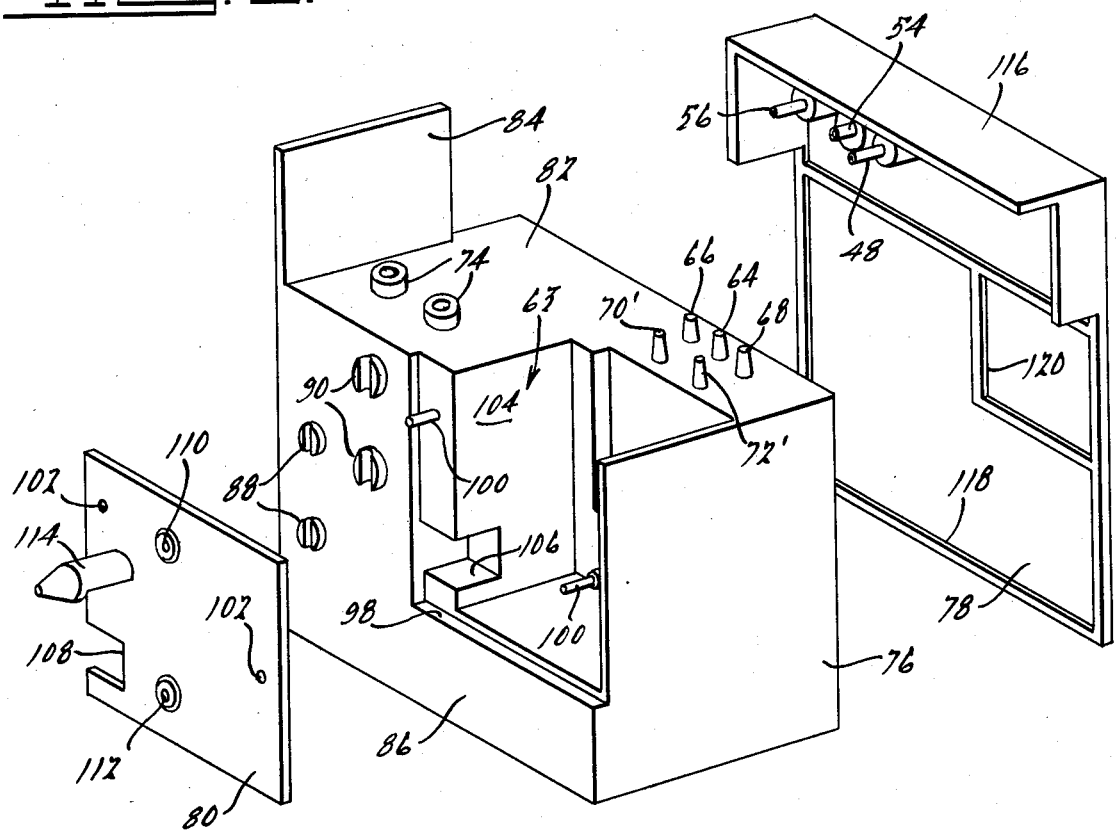
Fig. 10.

OPHTHALMIC CASSETTE

BACKGROUND AND SUMMARY OF THE INVENTION

The present invention relates generally to microsurgical equipment and systems, especially those used in ophthalmic surgery. More particularly, the invention relates to a cassette apparatus for collecting substances removed from a surgical situs by suction. The cassette is adapted for removable connection to a control console and provides fast aspiration response time from a single vacuum source.

Present day microsurgical systems for performing ophthalmic surgery typically provide one or more handheld instruments attached to and operated by a control console. The instruments typically are a vitreous cutting probe or a suction cannula. The probe or cannula are usually provided with a hollow needlelike tip through which the substances removed from the surgical situs are suctioned into a removable, throwaway cassette. The control console houses an adjustable vacuum source for providing the aspiration suction to the probe or cannula, and also includes a pneumatic driver system for causing the shearing or rotary cutting action of the probe tip.

In practice, the probe or cannula are coupled through a length of plastic tubing to the cassette collection container and a vacuum is drawn in the container by the variable vacuum source when aspiration is required. One problem encountered in microsurgical systems of this type is that the comparatively slow vacuum rise time in the collection receptacle make it difficult to precisely control the aspiration desired. In eye surgery this is particularly crucial, since aspiration must be precisely controlled to remove only diseased tissue without damaging adjacent healthy tissue. Generally speaking, the ideal aspiration system would have a very fast vacuum rise time and a similarly fast fall time or turn off time. This ideal has been difficult to achieve due to the inertia of the fluid system which includes the aspirator. To an appreciable extent, this inertia is due to the volume of the collection container and the comparatively long time needed to effect a pressure change in that container.

As one solution to the aforementioned vacuum rise time problem, one aspiration system uses a double collection bottle arrangement in which a small bottle is used during aspiration for the rapid response time which the small volume allows. To overcome the problem of having the small bottle fill up too quickly, a second, larger bottle is coupled to the small bottle and a second (frequently more powerful) vacuum source is provided for suctioning the contents of the small bottle into the large bottle as required to prevent overfilling of the small bottle. While generally workable, this two bottle, dual-vacuum system is overly complex, requiring the independent control of two separate vacuum sources. With greater complexity goes a greater likelihood of malfunction, hence, the dual-bottle, dual-vacuum system, leaves room for improvement.

The present invention provides the benefits of a dual-bottle collection system through a much simpler and more reliable arrangement which requires only one vacuum source. The present invention also provides a collection cassette which is less expensive to manufacture. The invention thus offers considerable improvement over prior microsurgical equipment.

Accordingly, the present invention provides a microsurgical apparatus for collecting substances removed from a surgical situs by suction. The invention comprises a fast rise time primary container having a means for selectively applying a vacuum thereto and having an inlet means for communicating with the surgical situs, typically through an aspirating cutting probe or cannula. The invention further comprises a secondary container of a capacity greater than the primary container. Both containers are integrally formed into a unitary, generally boxlike cassette. The containers are disposed so that a given quantity of the substance in the primary container has a greater potential energy than the same quantity of substance has in the secondary container. A first passage communicates between the primary and secondary containers to conduct substances from the primary to the secondary by gravity, thereby eliminating the need for a dual-vacuum system.

To maintain the fast rise time during aspiraion, a first valve is provided which opens and closes the first passage in response to vacuum pressures within the primary container. When vacuum is applied to the primary container, the valve is closed, maintaining the fast rise time of the primary container and preventing the down flush of substance into the secondary container. When the vacuum is removed from the primary container, the valve opens, permitting the automatic down flush or emptying of substances from the primary into the secondary container by gravity. The secondary container is vented to atmosphere while the primary container is provided with a vent valve which selectively opens to vent to atmosphere. This vent valve is opened during times when the aspiration vacuum is removed from the primary container, thereby equalizing the pressure in both containers and permitting rapid flushing from the primary to the secondary container. Preferably the invention employs a vacuum supply valve for selectively applying a vacuum to the primary container and an aspiration inlet valve for opening and closing the aspiration inlet. Both vacuum supply and aspiration inlet valves are arranged for substantially simultaneous operation. The vent valve is arranged for sychronized reverse operation relative to the aspiration inlet and vacuum supply valves. The vent valve is closed when the vacuum supply and aspiration inlet valves are open, and vice versa.

For a more complete understanding of the invention, its objects and advantages, reference may be had to the following specification and to the accompanying drawings.

BRIEF DESCRIPTION OF THE DRAWINGS

FIG. 1 is a front view of the microsurgical apparatus of the invention installed in a microsurgical control console;

FIG. 2 is a frontal perspective view of the cassette apparatus of FIG. 1;

FIG. 3 is a schematic view of the cassette of the invention, illustrating the various inlets, outlets and valve arrangements;

FIG. 4 is a left side elevational view of the cassette apparatus with the sidewall broken away;

FIG. 5 is a top plan view of the cassette assembly of the invention;

FIG. 6 is a rear elevational view of the cassette assembly of the invention, with a portion thereof broken away to better show the vacuum source connection ports and associated tubing;

FIG. 7 is a detailed vertical cross sectional view taken through the vacuum responsive valve, showing the valve membrane in the closed position;

FIG. 8 is a horizontal cross sectional view of the vaccum responsive valve taken substantially along the line of 8—8 in FIG. 7;

FIG. 9 is a vertical cross sectional view taken substantially along the line 9—9 of FIG. 4;

FIG. 10 is an exploded rear perspective view of the cassette with tubing removed; and FIG. 11 is a detailed vertical cross sectional view similar to FIG. 7, showing the valve membrane in the open position.

DESCRIPTION OF THE PREFERRED EMOBODIMENT

Referring to FIG. 1, the microsurgical cassette apparatus of the invention is illustrated generally at 20 detachably installed in a microsurgical control console 22. Although the configuration of the console may vary, the illustrated console includes a vacuum adjustment knob 24 which is used to adjust the maximum aspiration delivered to the probe or cannula upon full depression of a control footswitch (not shown). A digital display 26 is provided for indicating the maximum vacuum established by the setting on knob 24. Preferably the maximum aspiration level is adjustable by increments on the order of 10 mm Hg. Console 22 further includes a cassette release lever 28 which may be depressed to release cassette 20, allowing it to be removed from the console. Console 22 further includes a cutting probe actuator fitting 30 and cutting rate adjustment knob 32. A cutting probe 33 is attached to fitting 30 via a length of plastic tubing 34, and the cutting rate is read out on display 36 when the cutting mode has been engaged via the footswitch. Preferably the cutting rate is adjustable from nominally 300 to 600 cuts per minute. In addition, console 22 may include an illumination module 38, including light intensity control 40 and fiber optic light transmitting cable 42, which may be plugged into either the primary light source 44 or an alternate or interim light source 46 for providing illumination at the surgical situs during surgery.

Cassette 20 provides a vacuum port 48 for connection to the aspiration port 50 of probe 33 via plastic tubing 52. Cassette 20 also includes a pair of auxiliary ports 54 and 56 which may be connected, if desired, to provide auxiliary irrigation or aspiration functions.

FIG. 2 illustrates the cassette 20 when removed from the console 22. FIG. 10 illustrates the same cassette viewed from the back side (exploded and with tubing removed). As illustrated, the cassette defines a generally box-shaped locus defined by its outer exterior 58. The cassette is sized and shaped for slidable insertion into a corresponding rectangular opening in console 22. Preferably, cassette 20 is fabricated from transparent polystyrene plastic so that the microsurgeon can observe the levels and contents of fluids and other substances deposited in the cassette during surgery.

Cassette 20 integrally defines a generally box-shaped primary container 60 and a larger secondary container 62 (both seen through the transparent walls of exterior 58 in FIG. 2). Secondary container 62 encloses a substantially larger volume than primary container 60, and container 62 is disposed generally below primary container 60. This relationship is perhaps best seen in FIG. 9. Cassette 20 also defines a utility chamber 63 which is preferably open at the top.

Communicating with primary container 60 through the top wall thereof are three ports: a vacuum port 64 for connection to a source of vacuum within control console 22, an aspirant inlet port 68 for connection to vacuum port 48 and a vent port 66. In addition, primary container 60 is provided with a pair of level sensing electrodes 70 and 72 which also enter through the top of primary container 60. Secondary container 62 is provided with a pair of vents 74 which maintain that container at atmospheric pressure.

With specific reference to FIG. 10, cassette 20 is preferably formed from injection molded interfitting components. Cassette 20 comprises a generally box-shaped body component 76, a cover component 78 and a utility panel component 80. The top wall 82 of body component 76 is formed with upwardly extending ports 64, 66 and 68. Top wall 82 is also formed with upwardly extending stacks which comprise vents 74. Electrodes 70 and 72 also protrude upwardly from top wall 82. Preferably, electrodes 70 and 72 take the form of electrically conductive straight pins inserted into or encapsulated in electrode risers 70' and 72'. Top wall 82 is also provided with an upstanding partition wall 84, which defines the uppermost extent of the cassette's exterior.

The rear wall 86 of body component 76 includes a first pair of plastic tubing support members 88, and a second pair of plastic tubing support members 90. Support members 88 are sized to frictionally or resiliently grip a length of flexible tubing, such as vent tubing 92 (FIG. 6). Support members 90 are adapted to accommodate two side-by-side lengths of tubing, such as aspiration tubing 94 and vacuum tubing 96 (FIG. 6). The precise interconnection of the various lengths of tubing will be discussed more fully below. Rear wall 86 is provided with a generally rectangular recessed region 98 which is adaped to receive utility panel component 80. Panel component 80 is held in place by two studs 100 which fit into corresponding holes 102 on panel component 80 and are heat stake riveted together.

Body portion 86 and panel component 80 together define the utility chamber 63. Utility chamber 63 encloses a plurality of individual lengths of tubing, including vent tubing 92, aspirant tubing 94 and vacuum tubing 96. To provide a duct for routing tubing 92, 94 and 96 from the exterior of rear wall 86 into the interior of utility chamber 63, inner vertical wall 104 of body component 76 is provided with inset duct space 106. Duct space 106 aligns with a rectangular notch or cutout 108 in component 80 to provide a duct through which tubing 92, 94 and 96 is routed (see FIG. 6). Utility panel component 80 is also provided with a pair of vacuum source fittings 110 and 112 and an outwardly protruding latching member 114. Latching member 114 is positioned to interconnect with conventional latching hardware within console 22 for releasably securing the cassette in the console in the usual fashion. Vacuum source fittings 110 and 112 are positioned for mating interconnection with the conventional vacuum supply fittings within console 22 (not shown).

Integrally formed on cover component 78 is vacuum port 48 and auxiliary ports 54 and 56. The cover component is provided with an upper cowling 116 which overhangs and protects ports 48, 54 and 56 while also protecting ports 64, 66 and 68. When cover component 78 is assembled on body component 76, upper cowling 116, together with partition wall 84, defines the uppermost extent of the cassette's box-shaped exterior. Cover component 78 is provided with a generally rectangular seal forming outer edge 118, which mates with a corresponding rectangular periphery of body component 76 to define secondary container 62. Cover component 78 is further provided with a second rectangular seal forming edge 120 which mates with the sidewalls of primary container 60. Once assembled, cover component 68 and panel component 80 may be permanently secured to body component 78 by ultrasonic welding, gluing, or any other conventional means.

With reference to FIGS. 3 through 6, the interconnection of various lengths of plastic tubing may be seen. For convenience, reference may be had to FIG. 3 which illustrates the invention schematically. The invention is capable of being operated from a single vacuum source. However, since some microsurgical consoles provide dual vacuum sources, cassette 20 provides two vacuum source fittings 110 and 112. Vacuum source fitting 110 is adaped for direct coupling to a vacuum source within console 22. This fitting is the principal vacuum connection fitting for the cassette and is used where the console provides only one vacuum source. Vacuum source fitting 112 serves as the secondary vacuum connection fitting and is provided with a check valve 122. Vacuum source fitting 110 and check valve 122 both connect to a T-fitting 124 and the T-fitting is in turn connected to one end of vacuum tubing 96. Tubing 96 is routed upwardly through the open top of utility chamber 63 and is then passed through tubing supports 90, routed through cutout 108 and connected to vacuum port 64 on primary container 60. Check valve 122 closes vacuum source fitting 112 when a single vacuum source is connected to fitting 110. This prevents vacuum loss through fitting 112 and permits the invention to be used with single vacuum source consoles. When two vacuum sources are connected to fittings 110 and 112, the two vacuum sources act in concert to draw a vacuum in primary container 60.

Also connected to primary container 60 at the aspiration inlet port 68 is aspiration tubing 94. Tubing 94 is routed down through the open top of utility chamber 63, out through cutout 108 and then through tubing supports 90 for connection to vacuum port 48. Aspiration tubing 94, thus, communicates between the probe 33 and primary container 60. Plastic tubing supports 90 hold the aspiration tubing 94 and vacuum tubing 96 in side by side relation to one another directly adjacent rear wall 86. Console 22 may be provided with a valve actuator which operates to open and close the fluid passageways provided by tubing 94 and 96. In one embodiment, a plunger 126 (shown diagrammatically in FIG. 3) is positioned above tubing 94 and 96 in the space between tubing supports 90. The plunger closes or blocks tubing 94 and 96 by depressing or squeezing the tubing against adjacent rear wall 86, flattening the tubing so it will not conduct fluid. Plunger 126 is held in normally open (N.O.), spaced relation to tubing 94 and 96, so that fluid flow through the tubing is normally permitted. Preferably, tubes 94 and 96 are arranged for simultaneous operation, i.e., tubing 94 and 96 are both blocked or opened substantially simultaneously.

In a similar fashion, vent port 66 is coupled to vent tubing 92, which is routed through the open top of utility chamber 63, out through cutout 108 and up through plastic tubing supports 88. A second plunger 128 (FIG. 3) is positioned above tubing 92 in the space between tubing supports 88 for selectively opening and blocking vent tubing 92. Plunger 128 is held by the control console 22 in a normally blocking or closed position (N.C.) whereby vent tubing 92 is squeezed against rear wall 86. This ensures that primary container 60 is normally sealed from atmosphere. Plungers 126 and 128 act as valves for selectively opening and closing vent tubing 92, aspirant tubing 94 and vacuum tubing 96. As indicated, plunger 126 acts as a normally open (N.O.) valve while plunger 128 acts as a normally closed (N.C.) valve. In this case, the valve action is produced by the squeezing of the plastic tubing against rear wall 86, which flattens the tubing sufficiently to block its internal passageway. If desired, other types of valves may be utilized. If this is done, plungers 126 and 128 may be used to actuate the valves, or they may be eliminated entirely if the valves are capable of actuation by electrical signals.

As best seen in FIGS. 7, 8 and 9, primary container 60 and secondary container 62 are coupled to one another through standpipe conduit 130. Conduit 130 is provided with a vacuum responsive valve 132 which closes when a vacuum is applied to container 60, thereby preventing fluid communication between chambers 60 and 62. Valve 132 opens when the vacuum in container 60 is released, thereby permitting the downflush of fluid and other suspended substances from container 60 into container 62 by the force of gravity. As seen in FIG. 9, the lowermost wall 134 of primary container 60 is elevated above the lowermost wall 136 of secondary container 62. Thus, a given quantity of substance within container 60 is at a higher potential energy than the same quantity of substance in container 62. When valve 132 is open, substances in container 60 will flush downwardly through conduit 130 under gravitational forces in order to seek a state of lower potential energy.

Valve 132 is preferably a form of flapper valve best seen in FIGS. 7, 8 and 11. Referring first to FIG. 7, standpipe conduit 130 is provided with an annular flared end 138 which has a pair of downwardly depending concentric hubs 140 and 142. Carried on hub 140 is a cap 144 which is provided with a circular opening 146 in the bottom thereof. Sandwiched between hub 140 and cap 144 is a valve membrane 148. As seen in FIG. 8, membrane 148 is provided with a C-shaped annular aperture 150 which defines a bridge portion 152. Bridge portion 152 acts as a flexible hinge to allow valve membrane 148 to move between the closed position shown in FIG. 7 and the open position in FIG. 11. In the closed position, membrane 148 is drawn upwardly in response to vacuum forces applied via primary container 60. In the closed position, membrane 148 makes sealing contact with concentric hub 142. In the open position, valve membrane 148 deflects to the lower position shown in FIG. 11 under the weight of substances in the standpipe and primary container directly above. With membrane 148 in the open position, substances may flow from the standpipe into the secondary container as indicated by the arrows 149 in FIG. 11. Access to the valve 132 may be had by removing cover 154 which is adapted for sealing engagement with lower wall 136.

In operation, cassette 20 is inserted into console 22, and in so doing, the appropriate connection of a vacuum source to fitting 110 is made. (If two vacuum sources are provided, then the appropriate connection is also made to fitting 112). Latching member 114 engages a catch within console 22 to hold cassette 20 in place. Next, probe 33 is connected by attaching tubing 34 to the cutting probe actuator 30, and by connecting tubing 52 between the probes aspiration port 50 and vacuum port 48 on the cassette. The desired aspiration vacuum is then set by adjusting knob 24 while viewing digital display 26. The cassette is now ready for use.

When aspiration is required, the surgeon will activate the aspiration mode, typically by depressing a foot switch (not shown) connected to the console. The aspiration mode is initiated by urging plunger 128 to the closing position which seals off vent tubing 92. At the same time, plunger 126 is urged to the open position, allowing a vacuum to be drawn in the primary container 60. The vacuum within container 60 causes valve 132 to close, sealing primary container 60 from secondary container 62. The vacuum rise time is, thus, responsive only to the volume within the smaller primary container 60. The larger secondary container 62, being sealed off, does not contribute to the vacuum rise time. As required, the surgeon directs the needlelike tip of probe 33 (or cannula) at substances to be removed. These substances are suctioned through the hollow tip and tubing 52 into the primary container 60 via vacuum port 48. From time to time, the surgeon may turn off the aspiration mode by foot switch control. Each time the aspiration mode is turned off, plunger 126 is urged to the closing position, which immediately disconnects vacuum to container 60 while simultaneously decoupling aspiration tubing 94 from the primary container. As a result, the vacuum fall time experienced at the surgical situs is quite rapid. Because the aspiration tubing is blocked at the inlet to primary container 60, the response time during shutoff is responsive only to the volume within tubing 52 and that portion of tubing 94 between vacuum port 48 and plunger 126.

Simultaneously with the actuation of plunger 126, plunger 128 is urged to the opening position. This vents the primary container 60 to atmosphere. Secondary container 62 is normally maintained at atmospheric pressure through vents 74. Thus, by opening vent tubing 92 to atmosphere, the pressure is equalized between primary container 60 and secondary container 62. With pressure equalized, substances within container 60 are free to fall or flush under the force of gravity through standpipe conduit 130 for discharge into the secondary container 62. The cassette of the invention, thus, provides a fast rise time primary container and an automatic gravity flush emptying of the primary container for extended use.

As a safeguard against over filling of container 60, electrodes 70 and 72 have tips which are disposed a predetermined distance above the lower wall 134 of container 60. The electrodes 70 and 72 are electrically coupled to a voltage source within console 22, and when the level of substance within container 60 rises to the electrode tips, an electrical current begins to flow from one electrode to the other, through the substance within container 60. This current flow is sensed by console 22 which may then perform an automatic flushing sequence whereby plunger 126 moves to the closing position and plunger 128 moves to the opening position, both for a predetermined flushing cycle time.

While the invention has been described in its presently preferred embodiment, it will be understood that the invention is capable of modification and change without departing from the spirit of the invention as set forth in the appended claims.

What is claimed as novel is as follows:

1. A microsurgical apparatus for collecting substances removed from a surgical situs by suction comprising:
   a primary container having means for selectively applying a vacuum thereto and having inlet means for communicating with said surgical situs;
   a secondary container of a capacity greater than said primary container;
   first passage means communicating between said primary and secondary containers for conducting substances from said primary container to said secondary container by gravity; and
   first valve means responsive to the vacuum within said primary container for opening and closing said first passage means.

2. The apparatus of claim 1 further comprising a means for selectively equalizing the pressure between said primary and secondary containers.

3. The apparatus of claim 1 wherein said secondary container is vented to atmosphere.

4. The apparatus of claim 1 wherein said secondary container is vented to atmosphere and said primary container has second valve means for selectively venting said primary container to atmosphere.

5. The apparatus of claim 1 further comprising second valve means for selectively opening and closing said inlet means.

6. The apparatus of claim 1 further comprising second valve means for selectively opening and closing said inlet means and wherein said means for selectively applying a vacuum comprises second passage means for coupling to a source of vacuum and third valve means for selectively opening and closing said second passage means.

7. The apparatus of claim 6 wherein said second and third valve means are arranged for substantially simultaneous operation.

8. The apparatus of claim 1 wherein said primary and secondary containers share at least one common substance containment wall.

9. The apparatus of claim 1 wherein said primary and secondary containers each have a lowermost containment wall and said lowermost containment wall of said primary container is elevated above said lowermost containment wall of said secondary container.

10. A microsurgical apparatus for collecting substances removed from a surgical situs by suction comprising:
    a cassette integrally defining a primary container and integrally defining a secondary container of greater capacity than said primary container;
    a means for applying a vacuum to said primary container and an inlet means for communicating between said primary container and said surgical situs; and
    first passage means communicating between said primary and secondary containers having first valve means responsive to the vacuum within said primary containers;
    said containers being disposed such that a given quantity of substance in said primary container has a greater potential energy than the same quantity of substance has in said secondary container.

11. The apparatus of claim 10 further comprising a means for selectively equalizing the pressure between said primary and secondary containers.

12. The apparatus of claim 10 wherein said secondary container is vented to atmosphere.

13. The apparatus of claim 10 wherein said secondary container is vented to atmosphere and said primary container has second valve means for selectively venting said primary container to atmosphere.

14. The apparatus of claim 10 further comprising second valve means for selectively opening and closing said inlet means.

15. The apparatus of claim 10 further comprising second valve means for selectively opening and closing said inlet means and wherein said means for selectively applying a vacuum comprises second passage means for coupling to a source of vacuum and third valve means for selectively opening and closing said second passage means.

16. The apparatus of claim 10 wherein said second and third valve means are arranged for substantially simultaneous operation.

17. The apparatus of claim 10 wherein said primary and secondary containers share at least one common substance containment wall.

18. The apparatus of claim 10 wherein said primary and secondary containers each have a lowermost containment wall and said lowermost containment wall of said primary container is elevated above said lowermost containment wall of said secondary container.

19. The apparatus of claim 10 wherein said cassette defines a generally box-shaped locus and said primary and secondary containers are confined witin said locus.

20. The apparatus of claim 10 wherein said primary container is generally box-shaped having a bottom wall and at least one side wall in common with said secondary container.

* * * * *